United States Patent [19]

Trimmer et al.

[11] 4,245,648
[45] Jan. 20, 1981

[54] METHOD AND APPARATUS FOR MEASURING BLOOD PRESSURE AND PULSE RATE

[76] Inventors: Gordon A. Trimmer, 3030 Buckinghammock Trail; Edward W. Slechta, P.O. Box 1987, both of Vero Beach, Fla. 32960

[21] Appl. No.: 943,915

[22] Filed: Sep. 20, 1978

[51] Int. Cl.³ .............................................. A61B 5/02
[52] U.S. Cl. ................................... 128/680; 128/672; 128/689
[58] Field of Search ............... 128/687, 672, 700, 900, 128/677, 680, 681, 689; 73/141 A

[56] References Cited

U.S. PATENT DOCUMENTS

| | | | |
|---|---|---|---|
| 2,658,505 | 11/1953 | Sheer | 128/672 |
| 3,090,377 | 5/1963 | Salisbury et al. | 128/677 |
| 3,095,872 | 7/1963 | Tolles | 128/672 |
| 3,132,643 | 5/1964 | Baum et al. | 128/672 |
| 3,734,086 | 5/1973 | Phelps, Sr. | 128/700 |

Primary Examiner—Willis Little
Attorney, Agent, or Firm—Duckworth, Hobby & Allen

[57] ABSTRACT

The system of the present invention includes a sensor head which is coupled to an exteriorized artery. The sensor head includes electromechanical transducers at first and second locations which convert each periodic arterial pulse pressure wave passing the first and second locations into first and second periodic electrical waveforms. Electronic circuitry analyzes the first and second periodic electrical waveforms to determine the rise time of each periodic waveform produced by the first and second transducers. This electronic circuitry also analyzes the first and second periodic waveforms to determine the transit time of each pulse pressure wave between the first and second locations. An electronic computer utilizes the rise time and transit time data and certain calibration data to determine and display systolic pressure, diastolic pressure, and pulse rate immediately following each pulse pressure wave. The system of the present invention also computes and displays fifteen beat moving average values of the systolic pressure and diastolic pressure.

28 Claims, 7 Drawing Figures

METHOD AND APPARATUS FOR MEASURING BLOOD PRESSURE AND PULSE RATE

BACKGROUND OF THE INVENTION

1. Field of the Invention

The present invention relates to a method of and apparatus for measuring arterial blood pressure and pulse rate.

2. Description of the Prior Art

Blood pressure levels are typically measured manually by use of a sphygmomanometer wrapped around an individual's arm. This device includes a pressure gauge and an inflatible cuff which terminates the flow of blood through an artery during the measurement process. A sphygmomanometer is incapable of providing a continuous read out of systolic and diastolic blood pressure levels.

A second type of blood pressure measurement device provides a continuous blood pressure read out and includes a pressure transducer which must be surgically implanted within an artery.

U.S. Pat. No. 2,658,505 (Sheer) discloses an arterial pulse wave velocity meter having a piezoelectric transducer which is coupled to an exteriorized artery. The transducer utilized in connection with this device generates electrical signals representative of the displacement of the artery wall and the rotational force imparted to a second element of the transducer. An electrical differentiating circuit is provided to obtain the rate of change of the displacement waveform. Additional circuitry is provided to measure the ratio between the differentiated values and the electrical signal created by torsional forces. This ratio is utilized to determine the velocity of the arterial pulse wave.

U.S. Pat. No. 3,132,643 (Baum) determines blood pressure by measuring the time lapse between an electrocardiac signal generated by the heart and a consequent pressure pulse measured at a remotely located point on the body.

U.S. Pat. No. 3,095,872 (Tolles) measures blood pressure by impressing continuous wave alternating pressure signals on a flow of arterial blood. Phase changes in the continuous wave modulation signal between two points spaced along the arterial blood stream are measured to determine relative blood pressure levels.

U.S. Pat. No. 3,734,086 (Phelps) discloses an apparatus for detecting, measuring and displaying the pulse propagation time from the heart to an extremity by non-invasive means.

U.S. Pat. No. 2,114,578 (Strauss) discloses an apparatus for visibly indicating the frequency and amplitude of the human pulse. A rubber compression bag is used in combination with a piezoelectric crystal to convert blood pressure pulsations into electrical impulses.

SUMMARY OF THE INVENTION

The present invention contemplates a blood pressure and pulse rate measurement system comprising means coupled to an exteriorized artery at first and second locations for converting each periodic arterial pulse pressure wave passing the first and second locations into first and second periodic electrical waveforms. Means coupled to the converting means measures the rise time of each of the first and second periodic waveforms. Means coupled to the converting means measures the transit time of each pulse pressure wave between the first and second locations. Means coupled to the rise time measuring means and to the transit time measuring means computes the systolic pressure, diastolic pressure and pulse rate corresponding to each pulse pressure wave.

DESCRIPTION OF THE DRAWING

The invention is pointed out with particularity in the appended claims. However, other objects and advantages together with the operation of the invention, may be better understood by reference to the following detailed description taken in connection with the following illustrations wherein:

DESCRIPTION OF THE PREFERRED EMBODIMENT

In order to better illustrate the advantages of the invention and its contributions to the art, the theory and operation of the present invention will be discussed and then a preferred hardware embodiment of the invention will be described in some detail.

The circulatory system monitor of the present invention is an externally applied, passive, non-invasive device which continuously monitors and displays systolic and diastolic blood pressures by analyzing the waveform shape and the propagation velocity of the cardiovascular pulse pressure wave as the primary determinants for the blood pressure amplitude and combines this amplitude determination with the results of direct pulse waveform time measurements and mathematical computations to calculate the systolic and diastolic values. Electrical output waveforms of a piezoelectric transducer in sensor head 12 are shown. As the result of other direct measurements and mathematical computations, the monitor of the present invention is also able to display the pulse rate.

In addition to transporting blood through the major arteries the circulatory system of vertebrates transmits a pulse pressure wave which originates in the heart as the left ventricle empties into the aorta. This pulse pressure wave travels at a speed in the vicinity of 275 inches per second along the major arteries. Empirical data indicates that a direct correlation exists between changes in blood pressure and changes in the propagation velocity of this pulse pressure wave.

Figure 1:
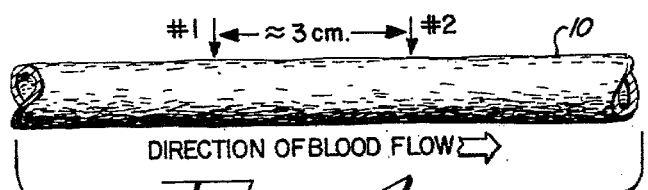
FIG. 1 illustrates the relative positioning of the first and second transducers with respect to the wall of an artery.
Figure 2:
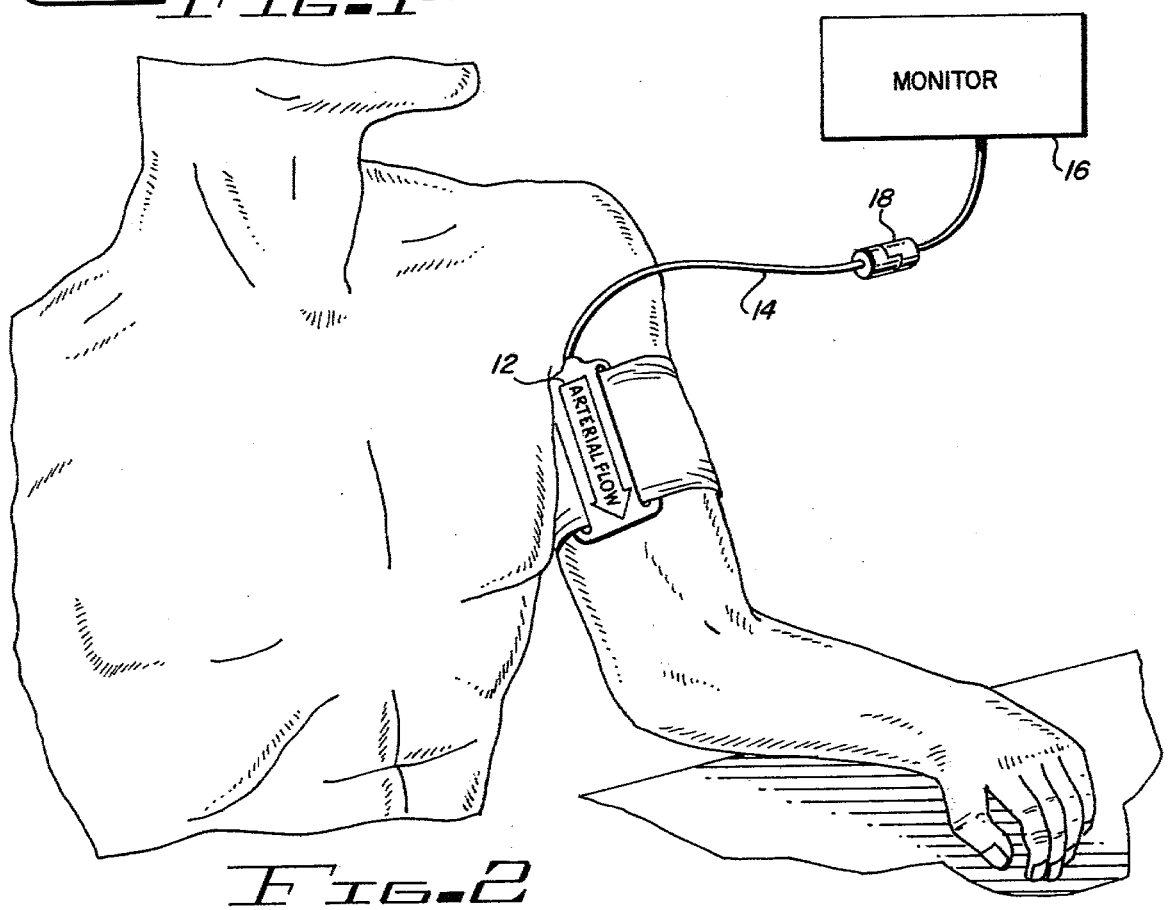
FIG. 2 indicates the general configuration of the sensor head of the present invention.

Referring now to FIGS. 1 and 2, an artery 10 transports a flow of blood in the direction indicated by the arrow. A pulse pressure wave having its origin at the heart propagates along artery 10 in the same direction as the blood flow. A sensor head 12 includes first and second electrodynamic transducers (not shown) on the lower surface thereof which are maintained at a fixed spacing of approximately three centimeters. The relative positioning of transducer number one with respect to transducer number two and artery 10 is indicated in FIG. 1. A Velcro strap is coupled to the body of the sensor head and is passed around the arm of the individual whose circulatory system is being monitored. Sensor head 12 is applied directly over and in alignment with the brachial artery on the inner portion of the upper arm. An adhesive material tightly couples the exposed portions of the first and second transducers to the skin layer lying between the artery and the transducer surfaces. In this manner relative displacement between sensor head 12 and artery 10 is virtually eliminated. A cable 14 couples sensor head 12 to an electronic computation and display module 16. A quick disconnect 18 may be provided between sensor head 12 and module 16 to permit sterile packaging of sensor head 12.

Most arteries contain a combination of elastic and muscular tissue. The structure of the major arteries near the aorta, however, is characterized by the absence of this muscular tissue which is the location for nerve endings causing cardiovascular constriction or dilation. As the arteries propogate outward from the aorta, they become more and more muscular and less and less "purely" elastic. Consistency in pulse pressure wave velocities and rise times for any particular value of blood pressure is enhanced by the placement of the sensor head on an exteriorized artery where the muscular tissue is least influential; i.e. on the brachial artery high on the arm.

Figure 3:
FIG. 3 is a graphical plot of blood pressure versus time.
Figure 4:
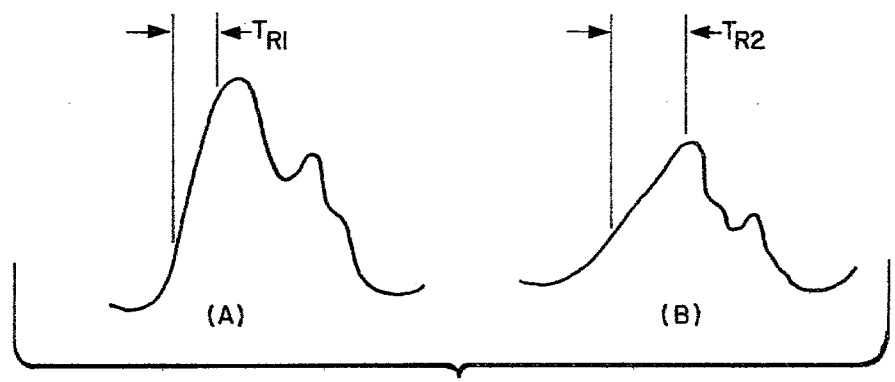
FIG. 4 illustrates plots of blood pressure versus time and arterial wall displacement versus time for a high blood pressure and a low blood pressure condition.

FIG. 3 indicates the variations in blood pressure with respect to time during a plurality of heartbeats. The maximum pressure during each heartbeat is referred to as the systolic pressure while the minimum blood pressure during each heartbeat is referred to as the diastolic pressure. Referring now to FIG. 4, a Diagram A represents the plot of a cardiovascular pulse pressure waveform having a comparatively high blood pressure excursion between the diastolic and systolic pressures and corresponds to a high pressure wave velocity. Diagram B illustrates the pressure plot of a lower pressure excursion between the diastolic and systolic pressures and a correspondingly lower pulse pressure wave velocity.

The present invention measures the rise times ($T_R$) associated with the initial portion of each pulse pressure wave. A shorter rise time corresponds to a higher effective blood pressure reading while a comparatively longer rise time corresponds to a lower effective blood pressure reading as is indicated in FIG. 4. Since $T_R1$ is less than $T_R2$, the blood pressure plot illustrated in diagram A corresponds to a higher blood pressure than the blood pressure plot illustrated in diagram B.

Figure 5:
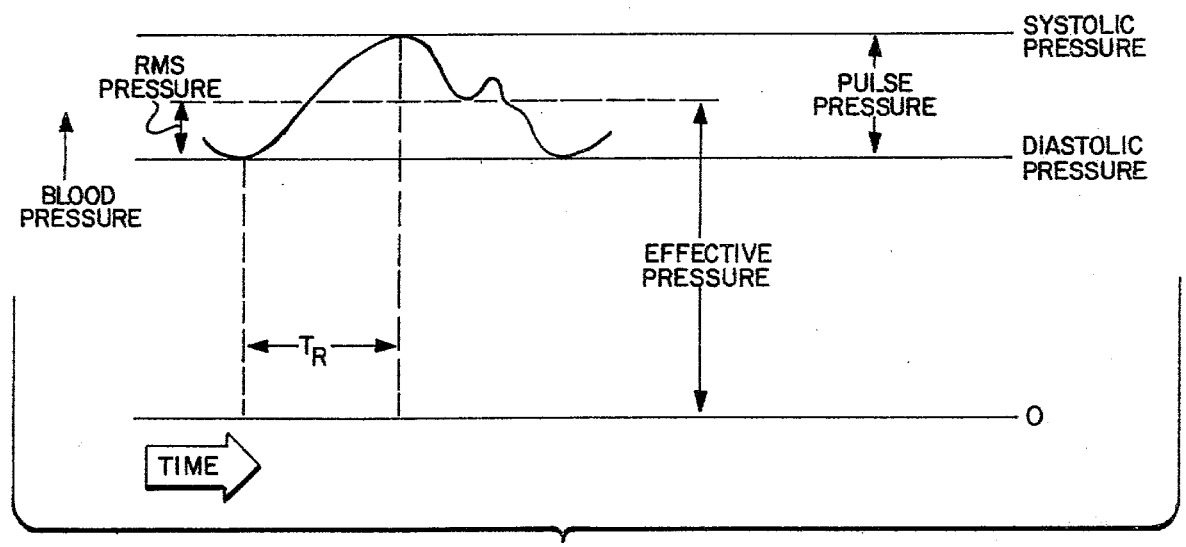
FIG. 5 defines a number of terms associated with a blood pressure waveform.

Referring now to FIG. 5, a plot of blood pressure versus time is illustrated. $T_R$ is equal to the time required for the blood pressure to increase from the diastolic pressure level to the systolic pressure level. The term "pulse pressure" (PP) is used to designate the pressure differential between diastolic and systolic pressure levels. The term "effective pressure" (EP) is defined to be that pressure which changes proportionally with changes in pulse pressure wave velocity, and is conincident with the root means square (RMS) pressure for the waveform generated by that pressure pulse. The RMS value for a pure sine wave is equal to 0.707. On the basis of calculations made from sample pulse pressure wave configurations, the RMS pressure value for a typical blood pressure wave of the type indicated in FIG. 5 will be about 0.656. This value varies from individual to individual.

In order to substantially simplify the explanation of a series of mathamatical computations which are performed by a computer positioned within module 16, a number of specialized terms will be defined as follows:

$T_R$—pulse pressure wave pressure rise time as measured by sensor number one in sensor head 12.

$T_R'$—pulse pressure wave pressure rise time measured by sensor number two of sensor head 12.

SP—systolic blood pressure measured in milimeters of mercury.

DP—diastolic blood pressure measured in milimeters of mercury.

PP—pulse pressure equal to SP minus DP.

HBR—heartbeat rate or pulse rate measured in beats per minute.

HBDT—delay time between heartbeats in second.

PPWTT—pulse pressure wave transit time in seconds required for a pulse pressure wave to propagate the three centimeter distance between sensors number 1 and 2 of sensor head 12. Pulse pressure wave velocity is equal to the reciprocal of PPWTT multiplied by a constant (k).

PWI—pulse wave intensity which is typically measured at 80 equal sample intervals during each waveform.

RMS (flow cal)—the computed RMS value of the blood pressure wave of a particular individual computed during the calibration process.

EP (flow cal)—The average or effective pressure driving a flow of blood through an artery. EP (flow cal) corresponds to the pressure wave velocity (k/PPWTT) during flow calibration.

EP (flow cal)+PP X RMS (flow cal)+DP.

The calibration procedure for the monitor must be accomplished prior to using the present invention for each different individual. Sensor head 12 is first attached to the brachial artery of an individual in accordance with the procedure set forth above. The monitor operator then checks the output indications on module 16 to ascertain that the sensor head has been properly positioned and that an appropriate output signal is being received.

As blood is flowing through artery 10, the rise times $T_R$ and $T_R'$ measured respectively by sensors one and two of sensor head 12 will be slightly different. The first part of the calibration procedure involves placing the monitor in the "no flow" calibration mode and positioning an inflatible calibration cuff downstream from sensor head 12. This calibration cuff is inflated to a pressure level sufficiently above the systolic pressure to terminate the flow of blood through artery 10. On the basis of the different arrival times of the pulse pressure waves at sensors one and two of sensor head 12, the computer within module 16 computes several consecutive PPWTT values, rejects any readings which deviate more than a predetermined value from the other readings and calculates a five beat average PPWTT value which shall be referred to as the PPWTT (no flow cal) value. This value is stored in the calibrate mode storage area of module 16. The values of $T_R$ and $T_R'$ are then measured during the calibration interval. Since as a result of electrical and other differences between transducers one and two the measured volumes of $T_R$ and $T_R'$ may not be exactly equal, the computer in module 16 multiplies $T_R'$ by an appropriate constant to cause $T_R'$ to be equal in magnitude to $T_R$. The value of $T_R$ measured during the no flow calibration interval is also stored in the calibrate mode storage and is designated $T_R$ (no flow cal). The constant which must be multiplied by $T_R'$ to cause it to be equal to $T_R$ during the calibration stages is also stored in memory as $T_R'$ (adjustment). The computer in module 16 automatically accomplishes all of the above described computation and storage procedures after the operator has placed the unit in the calibrate mode. Upon completion of the "no flow" calibration procedure, the operator then removes the calibration cuff which had terminated the flow of blood in artery 10. The monitor is then placed in the "flow" calibration mode and the operator proceeds to measure the systolic and diastolic pressures by applying a standard cuff type sphygmomanometer to the individual's arm over sensor 12. The cuff is inflated and deflated in the normal manner to determine SP and DP values. These values are entered by means of a keyboard on module 16 and are stored internally in memory. The sphygomomanometer cuff is now removed.

Immediately after receiving the SP and DP values from the operator, the computer in module 16 measures the values of PPWTT over a number of heartbeats. Values outside of a predetermined range are rejected and a five beat average value is computed. The computed value is compared with a predetermined range of allowable values and is rejected if it deviates excessively from those values. Once a proper value of PPWTT has been obtained it is entered in the calibrate mode storage as PPWTT (flow cal).

In a similar manner, a five beat moving average of the values for $T_R$ and $T_R'$ are obtained and the ration $(T_R-T_R')/T_R$ is computed and entered in the calibrate mode storage as $(T_R-T_R')/T_R$ (flow cal). After the calibration procedure, all measured values of $T_R'$ are multiplied by the correction factor $T_R'$ (adjustment).

Figure 6:
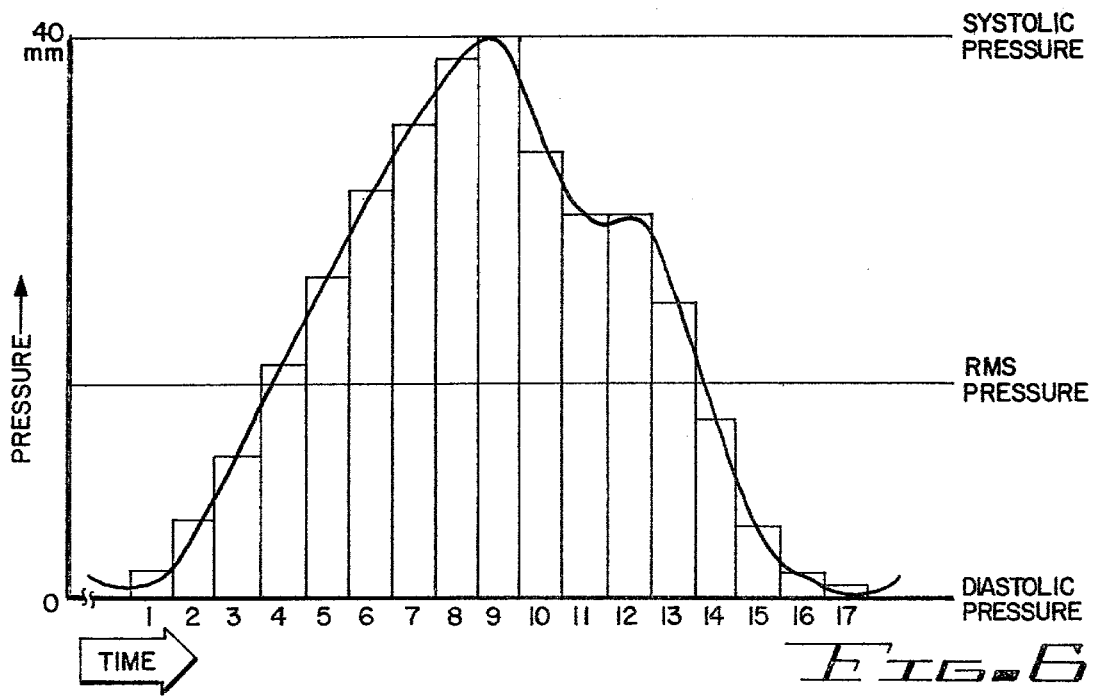
FIG. 6 indicates the method of determining root mean square pressure levels.

The value of the pulse wave intensity (PWI) is then calculated in the manner generally indicated in FIG. 6. The relative magnitude (diastolic pressure is assumed to be zero for the purpose of this computation) of the pulse pressure wave is computed at a number of sample intervals (eighty samples are taken in the preferred embodiment) over an entire pulse pressure wave. The value of each sample is squared and the sum of the squares of the values for an entire wave form is computed. The square root of the sum of the squares is designated as the RMS value of the waveform. The computer in module 16 computes a five beat moving average for the RMS value and this value is entered into the calibrate mode storage as RMS (flow cal). EP (flow cal) which is equal to RMS (flow cal) multiplied by the peak value of the pulse pressure wave is also averaged over five heartbeats and stored in the calibrate mode storage area. During normal operations, the RMS value of each waveform is computed. During the calibration process the latest five beat moving average value of HBDT is measured and entered in the calibrate mode storage areas as HBDT (flow cal).

The monitor is then placed in "monitor" mode and will now automatically and continuously display the pulse rate and both the most recent value and the fifteen beat moving average of the systolic and diastolic pressures. No further calibration steps are required as long as sensor head 12 remains in its original position.

The computer in module 16 now computes and displays the pulse rate by averaging the heartbeat delay time over the preceeding five heartbeats and taking the reciprocal of that value. This value is equal to the pulse rate and is displayed to the operator by module 16. The pulse rate in beats per minute is equal to 60/HBDT (average).

To obtain the other display outputs of module 16, HBDT, $T_R$ and $T_R'$, PPWTT and PWI (at 80 locations on the waveform) are measured for each pulse pressure wave which passes transducers one and two of sensor 12. A number of intermediate computations are performed by the computer in module 16 before the desired systolic pressure, diastolic pressure and pulse rate output can be displayed. A number of sophisticated corrections are applied in order to obtain readings of extremely high accuracy. These various computations and correction factors will now be discussed.

The proportional changes in rise times ($T_{RPC}$) are computed by solving the following equation.

$$T_{RPC}=(T_R-T_R')/T_R$$

A corrected rise time for each new pulse pressure wave is calculated by the computer within display module 16. This new value is indicated by the symbol $T_R$ (new corrected) and is computed by accomplishing the following computation:

$$T_R \text{ (new corrected)} = \quad (2)$$
$$T_R \text{ (new measured)} \times \frac{PPWTT \text{ (no flow cal)}}{PPWTT \text{ (new corrected)}} \times A$$
$$\text{Where } A = \left[ \frac{T_{RPC} \text{ (flow cal)}}{T_{RPC} \text{ (new)}} \Big/ \frac{HBDT \text{ (new)}}{HBDT \text{ (flow cal)}} \right] \quad (3)$$

A corrected value for PPWTT for each newly received pressure wave is then determined by accomplishing the following computation:

PPWTT (new corrected)=PPWTT (new measured)+Correction (new) \quad (4)

Where Correction (new)=Correction (flow cal)×$T_{RPC}$ (new)/$T_{RPC}$ (flow cal) \quad (5)

and where Correction (flow cal)=PPWTT (flow cal)−PPWTT (no flow cal) \quad (5A)

An updated EP value is computed for the most recent pulse pressure wave and is determined by performing the following computation:

$$EP \text{ (new)} = EP \text{ (flow cal)} \left[ \frac{PPWTT \text{ (no flow cal)}}{PPWTT \text{ (new corrected)}} \right] \quad (6)$$

The RMS value of the pulse wave intensity is then computed for the most recently received pulse pressure wave in the manner discussed in connection with FIG. 6. The pulse pressure (PP) corresponding to the most recently received pressure wave is determined by performing the following computation:

$$PP \text{ (new)} = PP \text{ (flow cal)} \times \frac{T_R \text{ (new corrected)}}{T_R \text{ (no flow cal)}} \quad (7)$$

where PP (flow cal) = SP (flow cal) − DP (flow cal) \quad (8)
— from keyboard input The diastolic pressure corresponding to the most recently received pressure wave is then determined by performing the following computation:

DP (new)=EP (new)−RMS value (new)×PP (new) \quad (9)

The systolic pressure corresponding to the most recently received pressure wave is then determined by performing the following computation:

$$SP (new) = DP (new) + PP (new) \quad (10)$$

While numerous different computations have been set forth above, only five variables are displayed by module 16 as used in connection with the preferred embodiment of the invention. The five beat moving average of the pulse rate is referred to as HBR (avg) and is displayed by monitor 16. The systolic and diastolic pressures for the latest heartbeat are displayed. The fifteen beat moving averages of the systolic and diastolic pressures are also displayed. Various intermediate computations as set forth above may be displayed in more elaborate versions of the present invention, however the above five readings are typically the most significant.

Figure 7:
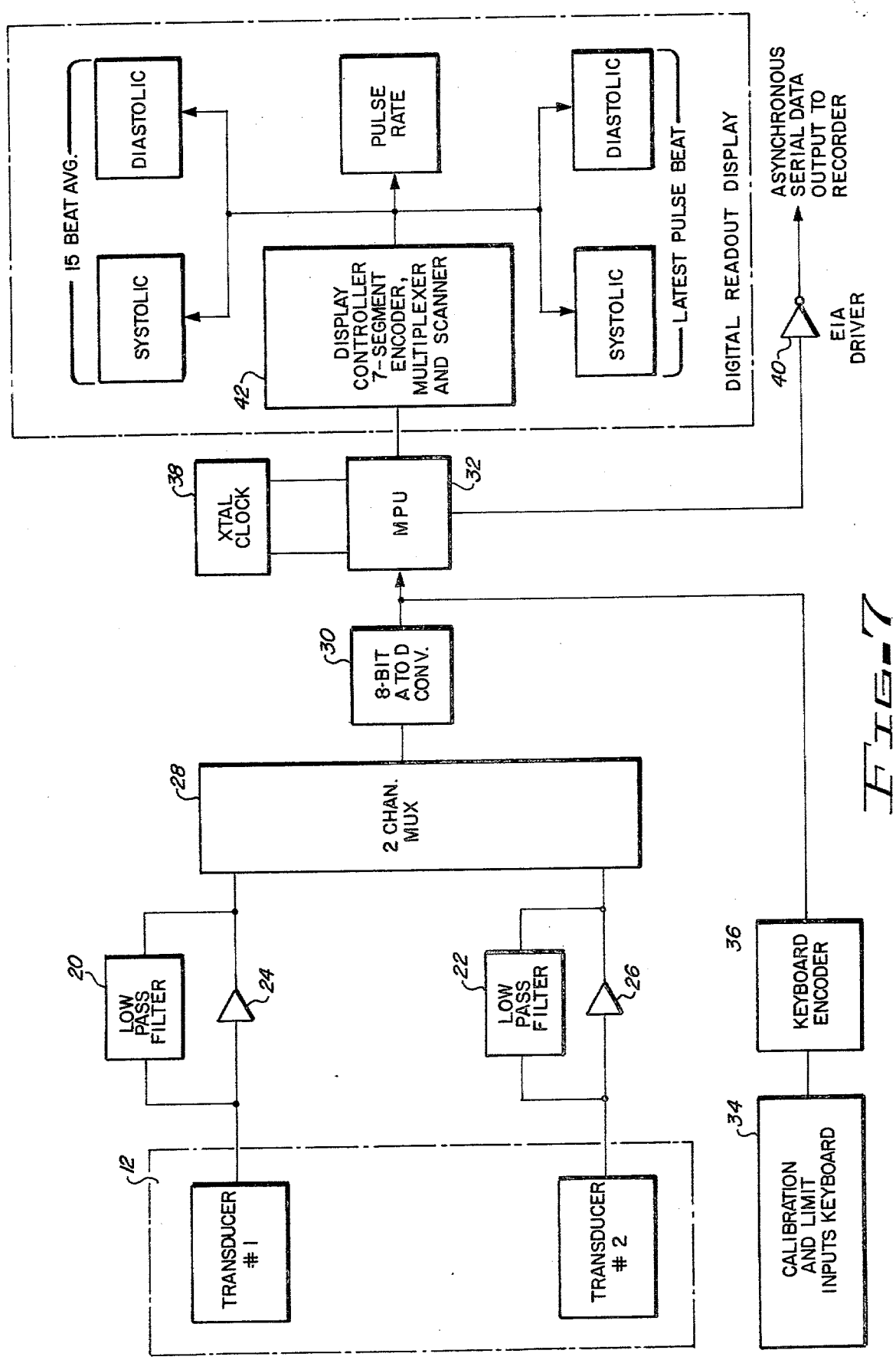
FIG. 7 is a block diagram showing the basic electronic elements of a preferred embodiment of the present invention.

Referring now to FIG. 7 a block diagram of the electronic components of the present invention will now be described. Transducers 1 and 2 of sensor head 12 generate electrical outputs each of which pass through low pass filters 20 and 22 which are coupled in series with amplifiers 24 and 26. The filtered, amplified outputs from transducers 1 and 2 are then coupled to two channel multiplexer 28 which provides a single multiplexed output to an eight bit analog to digital convertor 30.

Microprocessor 30 receives inputs from A/D converter 30 and from keyboard 34. Keyboard 34 is positioned on the front panel of module 16 and enables an operator to input various data such as measured systolic and diastolic pressures through keyboard encoder 36 to microprocessor 32.

A highly stable clock such as crystal clock 38 provides timing pulses to microprocessor 32. A selected output of microprocessor 32 may be coupled to driver amplifier 40 to permit the serial data output from the unit to be recorded on an accessory recording unit.

The method of programming microprocessor 32 to accomplish the mathematical computations and sequence of computations discussed above is well known to those skilled in the art.

Commercially available microprocessors such as the Intel 8080 or Motorola 6800 are readily adaptable for use in the present invention in a manner well known to those skilled in the art.

The output from microprocessor 32 is coupled to display controller 42 which includes a seven segment encoder, a multiplexer and a scanner. Display controller 42 drives a plurality of seven segment displays to indicate the fifteen beat moving average of the systolic and diastolic pressures, the systolic and diastolic pressures corresponding to the latest pulse beat and the current pulse rate. Each of these five displays is typically located on the front panel of module 16.

Keyboard 34 can also be used in connection with a plurality of alarms and warning lights which may be incorporated within module 16. This warning circuitry is incorporated to provide an audible and a visual alarm in the event that either the pulse rate or the systolic or diastolic pressures exceed predetermined limits. The operator enters the limit values in module 16 by depressing selected keys of keyboard 34. This warning feature may be desirable in certain applications of the present invention.

Since the monitor's fundamental measurements are expressed in time (in seconds), the success of the device is not dependent on consistency of amplitude received by the sensor head transducers, and therefore signal strength can vary with normal patient movements without affecting the accuracy of the monitor's output.

It will be apparent to those skilled in the art that the disclosed circulatory system monitor may be modified in numerous ways and may assume many embodiments other than the preferred forms specifically set out and described above. Accordingly, it is intended by the appended claims to cover all such modifications of the invention which fall within the true spirit and scope of the invention.

We claim:

1. A method for measuring blood pressure and pulse rate comprising the steps of:
   a. obtaining flow and no flow calibration data;
   b. passively measuring the rise times of each naturally occurring arterial pulse pressure wave at first and second locations separated by a predetermined distance;
   c. passively measuring the time required for each naturally occurring pulse pressure wave to travel between the first and second locations;
   d. determining the root mean square value of the pulse pressure waveform; and
   e. computing the systolic pressure, diastolic pressure and pulse rate for each naturally occurring pulse pressure wave.

2. The method of claim 1 further including the step of computing a multiple beat moving average value of systolic pressure and diastolic pressure.

3. The method of claim 1 further including the step of displaying the values of systolic pressure, diastolic pressure and pulse rate.

4. The method of claim 1 wherein the step of obtaining flow and no flow calibration data includes the step of measuring the systolic and diastolic blood pressures.

5. The method of claim 4 wherein the step of obtaining flow and no flow calibration data includes:
   a. terminating the flow of blood through the artery; and
   b. measuring the rise time of the arterial pulse pressure wave during the no flow condition.

6. The method of claim 1 including the further step of measuring the rise times of each arterial pulse pressure wave at repeatable points on the pulse pressure waveform produced by each sequential pulse pressure wave.

7. The method of claim 6 wherein the repeatable points occur between the minimum and maximum values of each pulse pressure waveform.

8. A blood pressure and pulse rate measurement system comprising:
   a. means coupled to an exteriorized artery at first and second locations for passively converting each naturally occurring periodic arterial pulse pressure wave passing the first and second locations into first and second periodic electrical waveforms;
   b. means coupled to said converting means for measuring the rise time of each of the first and second periodic waveforms;
   c. means coupled to said converting means for measuring the transit time of each pulse pressure wave between the first and second locations; and
   d. means coupled to said rise time measuring means and to said transit time measuring means for computing the systolic pressure, diastolic pressure and pulse rate for each pulse pressure wave.

9. The system of claim 8 wherein said converting means includes:
   a. a first electromechanical transducer at the first location for generating the first periodic electrical waveform; and
   b. a second electromechanical transducer positioned at the second location for generating the second periodic electrical waveform.

10. The system of claim 9 including:
   a. first low pass filter means coupled to the output of said first transducer for passing only the low frequency component of the first periodic electrical waveform; and
   b. second low pass filter means coupled to the output of said second transducer for passing only the low frequency component of the second periodic electrical waveform.

11. The system of claim 10 wherein said converting means includes analog to digital converter means coupled to the output of said first and second low pass filter means for converting the first and second periodic electrical waveforms into first and second digital signals.

12. The system of claim 8 further including means coupled to said computing means for visually displaying systolic pressure, diastolic pressure and pulse rate.

13. The system of claim 12 wherein said display means further includes:
   a. digital indicator means for displaying systolic pressure, diastolic pressure and pulse rate; and
   b. display controller means for receiving input data from said computing means and for controlling the operation of said digital indicator means.

14. The system of claim 8 wherein said computing means includes means for computing a multiple beat moving average value of the systolic pressure and diastolic pressure.

15. The system of claim 8 further including means coupled to said computing means for providing calibration data to said computing means and for designating limit inputs to said computing means.

16. The system of claim 15 further including alarm means coupled to said computing means for sounding an alarm when the systolic pressure, diastolic pressure or pulse rate deviate from predetermined limits.

17. The system of claim 8 wherein said computing means further includes a data recorder output.

18. The system of claim 9 wherein said first and second transducers are positioned in a sensor head.

19. The system of claim 18 wherein said first and second transducers within said sensor head are maintained at a predetermined fixed spacing.

20. The system of claim 19 wherein the predetermined fixed spacing between said first and second transducers is between two and ten centimeters.

21. The system of claim 19 wherein said first and said second transducers include piezoelectric crystals.

22. The system of claim 18 wherein said sensor head is maintained in position adjacent the exteriorized artery by attachment means.

23. The system of claim 22 wherein said attachment means includes a strap.

24. The system of claim 22 wherein the first and second transducers of said sensor head are adhesively secured to the exteriorized artery.

25. The system of claim 8 wherein said computing means includes a microprocessor.

26. The system of claim 9 wherein said first and second transducers are separately coupled to a single exteriorized artery.

27. The system of claim 26 wherein said first and second transducers are separated by a spacing in excess of ten centimeters.

28. The system of claim 24 wherein said first and second transducers are coupled to said exteriorized artery by a thin sheet of material having an adhesive layer on the upper and lower surfaces thereof.

* * * * *